(12) United States Patent
Tung et al.

(10) Patent No.: US 9,201,019 B2
(45) Date of Patent: Dec. 1, 2015

(54) ARTICLE EDGE INSPECTION

(71) Applicant: Seagate Technology LLC, Cupertino, CA (US)

(72) Inventors: David M. Tung, Livermore, CA (US); Joachim W. Ahner, Livermore, CA (US)

(73) Assignee: Seagate Technology LLC, Cupertino, CA (US)

( * ) Notice: Subject to any disclaimer, the term of this patent is extended or adjusted under 35 U.S.C. 154(b) by 37 days.

(21) Appl. No.: 14/096,002

(22) Filed: Dec. 3, 2013

(65) Prior Publication Data
US 2014/0354980 A1 Dec. 4, 2014

Related U.S. Application Data

(60) Provisional application No. 61/829,183, filed on May 30, 2013.

(51) Int. Cl.
*G01N 21/88* (2006.01)

(52) U.S. Cl.
CPC ..................... *G01N 21/88* (2013.01)

(58) Field of Classification Search
CPC .............. G01N 2021/4792; G01N 2020/556; G01N 2021/8864
USPC .......... 356/237.1–237.5; 250/559.29, 559.36, 250/559.41
See application file for complete search history.

(56) References Cited

U.S. PATENT DOCUMENTS

| 4,207,467 | A | 6/1980 | Doyle |
| 4,477,890 | A | 10/1984 | Mooney et al. |
| 4,551,919 | A | 11/1985 | Sakata et al. |
| 4,598,997 | A | 7/1986 | Auderset et al. |
| 4,618,773 | A | 10/1986 | Drukier |
| 4,794,550 | A | 12/1988 | Greivenkamp |
| 4,806,776 | A | 2/1989 | Kley |
| 4,975,571 | A | 12/1990 | McMurtry et al. |
| 5,058,178 | A | 10/1991 | Ray |
| 5,066,130 | A | 11/1991 | Tsukiji et al. |
| 5,131,755 | A | 7/1992 | Chadwick et al. |
| 5,168,322 | A | 12/1992 | Clarke et al. |
| 5,455,870 | A | 10/1995 | Sepai et al. |
| 5,610,392 | A | 3/1997 | Nagayama et al. |
| 5,627,638 | A | 5/1997 | Vokhmin |
| 5,661,559 | A | 8/1997 | Brezoczky et al. |

(Continued)

FOREIGN PATENT DOCUMENTS

| JP | 06-241758 A | 9/1994 |
| JP | 08-075661 A | 3/1996 |

(Continued)

OTHER PUBLICATIONS

Candela CS10, Optical X-BeamTM Surface Analyzer, Product Description (www.klatencor.com/defect-inspection/candela-cs10.html), accessed Apr. 17, 2013.

(Continued)

*Primary Examiner* — Hoa Pham

(57) ABSTRACT

Provided herein is an apparatus, including a photon emitting means for emitting photons onto surface edges of an article, a photon detecting means for detecting photons scattered from particles on the surface edges of the article, and a mapping means for mapping a particle or a defect of the surface of the article.

20 Claims, 10 Drawing Sheets

(56) References Cited

U.S. PATENT DOCUMENTS

Figure 1:
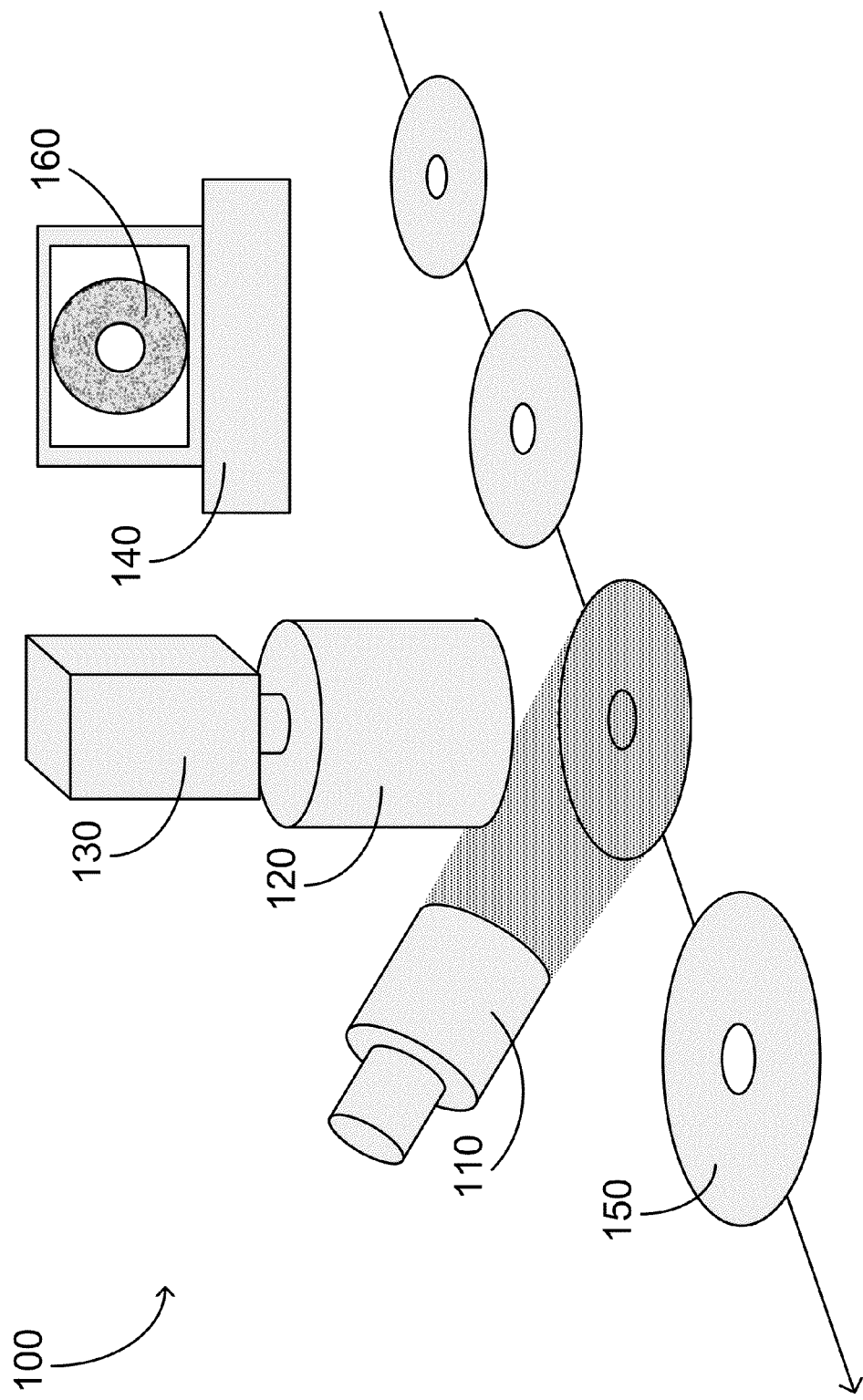

| | | |
|---|---|---|
| 5,726,455 A | 3/1998 | Vurens |
| 5,737,072 A | 4/1998 | Emery et al. |
| 5,774,212 A | 6/1998 | Corby, Jr. |
| 5,778,039 A | 7/1998 | Hossain et al. |
| 5,781,649 A | 7/1998 | Brezoczky |
| 5,859,698 A * | 1/1999 | Chau et al. ............ 356/237.2 |
| 5,898,491 A | 4/1999 | Horai et al. |
| 5,933,236 A | 8/1999 | Sommargren |
| 5,973,839 A | 10/1999 | Dorsel |
| 6,256,097 B1 | 7/2001 | Wagner |
| 6,392,745 B1 | 5/2002 | Mavliev et al. |
| 6,449,036 B1 | 9/2002 | Wollmann et al. |
| 6,476,908 B1 | 11/2002 | Watson |
| 6,483,584 B1 | 11/2002 | Lee et al. |
| 6,509,966 B2 | 1/2003 | Ishiguro |
| 6,515,742 B1 | 2/2003 | Ruprecht |
| 6,529,270 B1 | 3/2003 | Bills |
| 6,542,248 B1 | 4/2003 | Schwarz |
| 6,556,783 B1 | 4/2003 | Gelphman |
| 6,559,458 B2 | 5/2003 | Rinn |
| 6,559,926 B2 | 5/2003 | Yamaguchi et al. |
| 6,617,087 B1 | 9/2003 | Rangarajan et al. |
| 6,617,603 B2 | 9/2003 | Ishiguro et al. |
| 6,809,809 B2 | 10/2004 | Kinney et al. |
| 6,819,423 B2 | 11/2004 | Stehle et al. |
| 6,822,734 B1 | 11/2004 | Eidelman et al. |
| 6,847,907 B1 | 1/2005 | Novotny |
| 7,207,862 B2 | 4/2007 | Nabeya et al. |
| 7,433,031 B2 | 10/2008 | Xu et al. |
| 7,474,410 B2 | 1/2009 | Moon |
| 7,489,399 B1 | 2/2009 | Lee |
| 7,684,057 B2 | 3/2010 | Sakai |
| 7,751,609 B1 | 7/2010 | Berman |
| 7,777,876 B2 * | 8/2010 | Horai et al. ............ 356/237.3 |
| 7,969,567 B2 | 6/2011 | Yoshida et al. |
| 8,018,585 B2 | 9/2011 | Hariyama |
| 8,077,305 B2 | 12/2011 | Owen et al. |
| 8,139,232 B2 | 3/2012 | Wolf et al. |
| 8,223,326 B2 | 7/2012 | Kim et al. |
| 8,294,890 B2 | 10/2012 | Usuda |
| 8,547,545 B2 | 10/2013 | Sasazawa et al. |
| 2001/0036588 A1 | 11/2001 | Buschbeck et al. |
| 2002/0088952 A1 | 7/2002 | Rao et al. |
| 2004/0207836 A1 | 10/2004 | Chhibber et al. |
| 2004/0231177 A1 | 11/2004 | Mies |
| 2005/0067740 A1 | 3/2005 | Haubensak |
| 2005/0099204 A1 | 5/2005 | Uh et al. |
| 2005/0174575 A1 | 8/2005 | Norton et al. |
| 2005/0280808 A1 | 12/2005 | Backhauss et al. |
| 2006/0126062 A1 | 6/2006 | Tuschel |
| 2006/0147814 A1 | 7/2006 | Liang |
| 2006/0181700 A1 * | 8/2006 | Andrews et al. ............ 356/237.2 |
| 2007/0229852 A1 | 10/2007 | Wack et al. |
| 2008/0174771 A1 | 7/2008 | Yan et al. |
| 2008/0191137 A1 | 8/2008 | Poteet et al. |
| 2008/0309927 A1 * | 12/2008 | Grueneberg ............ 356/237.1 |
| 2009/0009753 A1 | 1/2009 | Horai et al. |
| 2009/0122304 A1 * | 5/2009 | Jin et al. ............ 356/237.4 |
| 2009/0320051 A1 | 12/2009 | Meerwald et al. |
| 2009/0323051 A1 | 12/2009 | Matsui |
| 2010/0053602 A1 * | 3/2010 | Hayashi et al. ............ 356/237.3 |
| 2010/0053603 A1 | 3/2010 | Sakaguchi et al. |
| 2010/0091272 A1 | 4/2010 | Asada et al. |
| 2011/0066382 A1 | 3/2011 | Adams |
| 2011/0141272 A1 | 6/2011 | Uto et al. |
| 2012/0140211 A1 | 6/2012 | Oshima et al. |
| 2012/0194808 A1 | 8/2012 | Oka et al. |
| 2013/0077159 A1 | 3/2013 | Tani |
| 2013/0198697 A1 | 8/2013 | Hotel et al, |
| 2013/0301040 A1 | 11/2013 | Ahner et al. |
| 2014/0043621 A1 | 2/2014 | Ahr:er, at al. |
| 2014/0098364 A1 * | 4/2014 | Ahner et al. ............ 356/237.2 |
| 2014/0098368 A1 | 4/2014 | Ahner et al. |
| 2014/0104604 A1 * | 4/2014 | Ahner et al. ............ 356/237.4 |
| 2014/0129179 A1 | 5/2014 | Xu et al. |
| 2014/0160481 A1 | 6/2014 | Ahner et al. |
| 2014/0354980 A1 * | 12/2014 | Tung et al. ............ 356/237.2 |
| 2014/0354981 A1 * | 12/2014 | Ahner et al. ............ 356/237.2 |
| 2014/0354982 A1 * | 12/2014 | Ahner et al. ............ 356/237.3 |
| 2014/0354984 A1 * | 12/2014 | Tung et al. ............ 356/237.5 |
| 2014/0354994 A1 | 12/2014 | Ahner et al. |

FOREIGN PATENT DOCUMENTS

| | | |
|---|---|---|
| JP | 08-178867 A | 7/1996 |
| JP | 2003-202214 | 7/2003 |
| JP | 3692685 B2 | 9/2005 |
| JP | 2006-30851 A | 11/2009 |
| JP | 2011-163872 A | 8/2011 |
| JP | 2012-026862 A | 2/2012 |
| JP | 2012-185121 A | 9/2012 |
| KR | 10-0763942 B1 | 10/2007 |
| KR | 10-0769342 B1 | 10/2007 |
| KR | 10-2011-021304 A | 3/2011 |
| WO | 96-05503 A1 | 2/1996 |

OTHER PUBLICATIONS

Candela CS20, Advanced Inspection for Compound Semiconductor and Optoelectronic Materials, Optical Surface Analyzer, KLA-TENCOR Corporation, 2010.

High-sensitivity, High-speed Dark-field Wafer-defect Inspection System-IS3000, Hitachi Review vol. 55, No. 2, pp. 73-77, Hitachi Ltd., 2006.

Hitachi High-Technologies I-5320 /I-6300—Electron Beam Wafer Inspection System, (www.etesters.com/listing/ea101bfb-1422-08df-aaae-08c275a8ee86/1-5320_-_I-6300_-_Electron_Beam_Wafer_Inspection_System), accessed Jun. 19, 2013.

Hitachi High-Technologies IS3000—Dark Field Wafer Defect Inspection System, (www.etesters.com/listing/ea1312b5-1422-08df-aa4b-5fea5982b63b/IS3000_-_Dark_Field_Wafer_Defect_Inspection_System), accessed Jun. 19, 2013.

Hitachi High-Technologies LS6800—Wafer Surface Inspection System, (www.etesters.com/listing/ea1133d4-1422-08df-aad9-258baeaf6c16/LS6800_-_Wafer_Surfce_Inspection_System), accessed Jun. 19, 2103.

LS Unpatterned Wafer Inspection System, (hitachi-htc.ca/products/semiconductor-metrology-equipment/inspections-systems/wafer-inspection-system/ls-unpatterne), accessed Jun. 19, 2013.

* cited by examiner

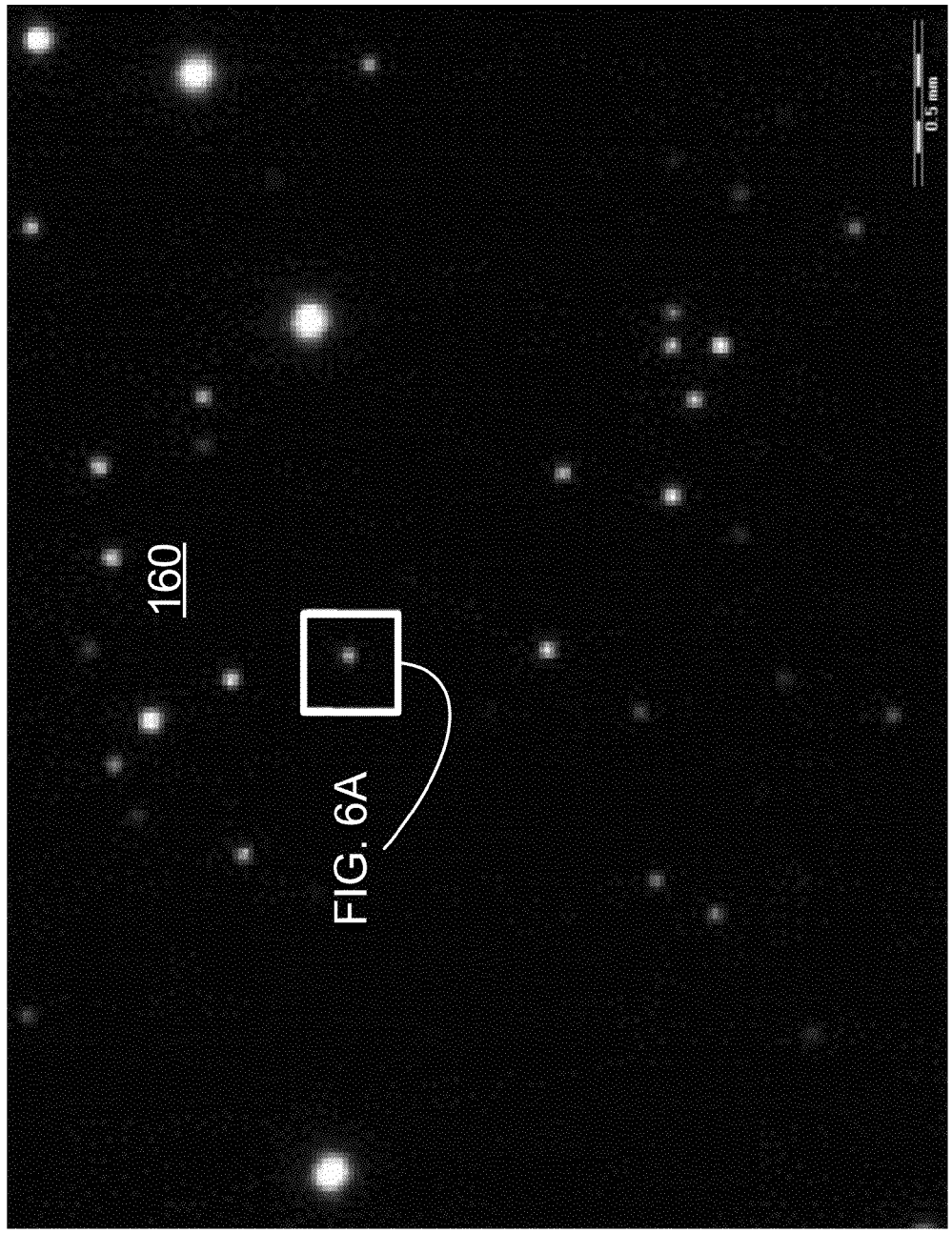

ARTICLE EDGE INSPECTION

CROSS REFERENCE

This application claims the benefit of U.S. Provisional Patent Application No. 61/829,183, filed May 30, 2013.

BACKGROUND

An article fabricated on a production line may be inspected for certain features, including defects that might degrade the performance of the article or a system comprising the article. For example, a hard disk for a hard disk drive may be fabricated on a production line and inspected for certain surface features, including surface and subsurface defects that might degrade the performance of the disk or the hard disk drive.

SUMMARY

Provided herein is an apparatus, including a photon emitting means for emitting photons onto surface edges of an article, a photon detecting means for detecting photons scattered from particles on the surface edges of the article, and a mapping means for mapping a particle or a defect of the surface of the article.

These and other features and aspects may be better understood with reference to the following drawings, description, and appended claims.

DRAWINGS

FIG. 1 provides a schematic illustrating detection of surface features of articles in accordance with an embodiment.

Figure 2:
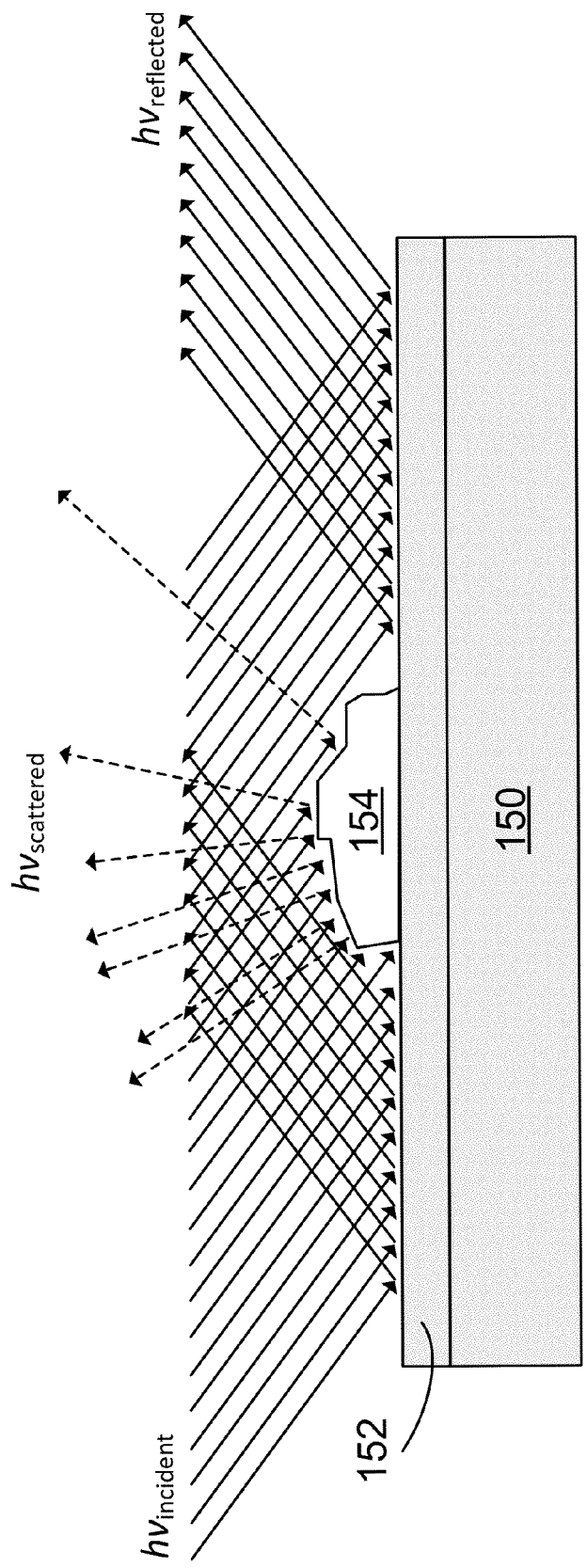

FIG. 2 provides a schematic illustrating photon scattering from a surface feature of an article in accordance with an embodiment.

Figure 3:
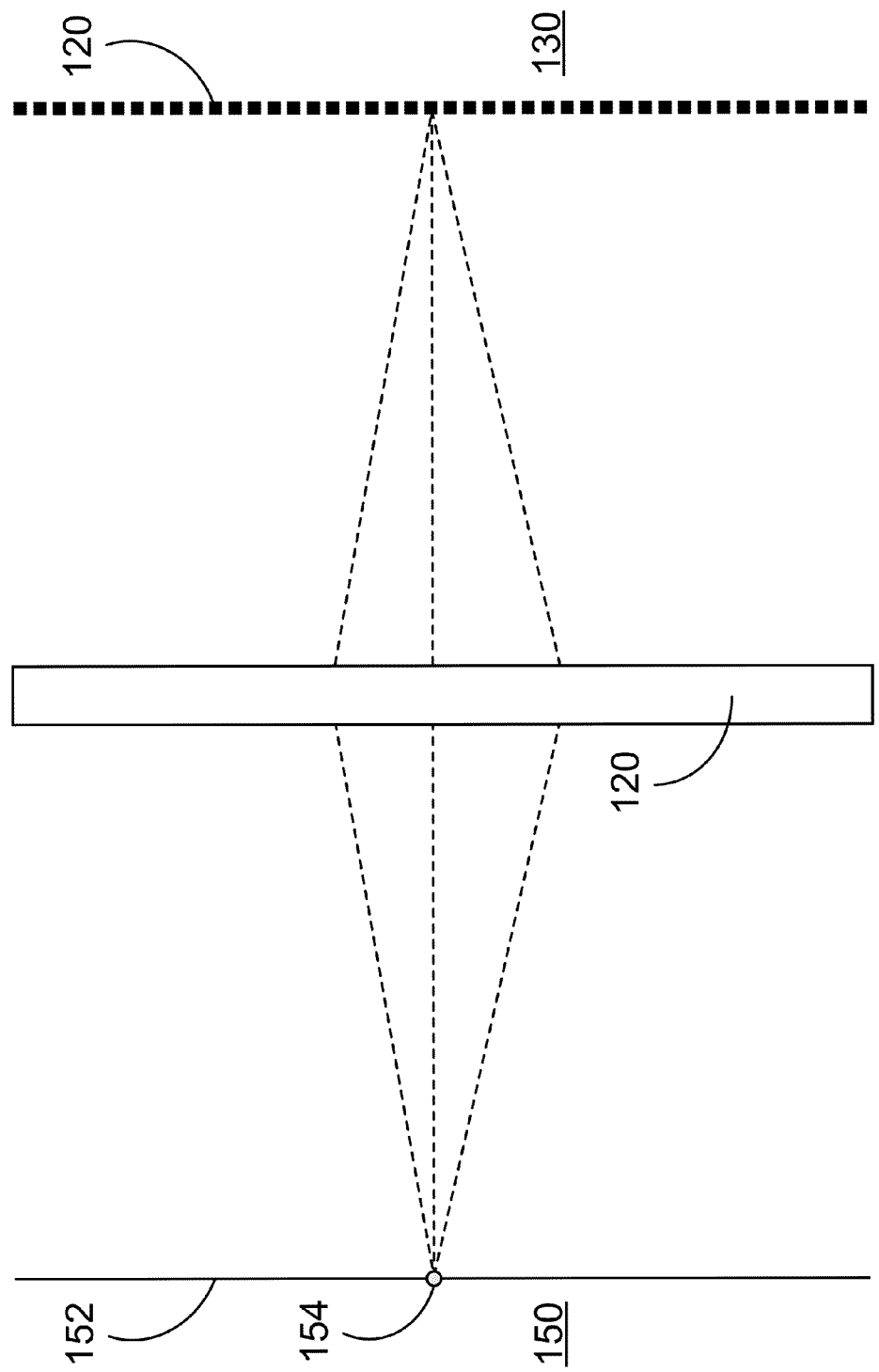

FIG. 3 provides a schematic illustrating photons scattering from a surface feature of an article, through an optical component, and onto a photon detector array in accordance with an embodiment.

Figure 4:
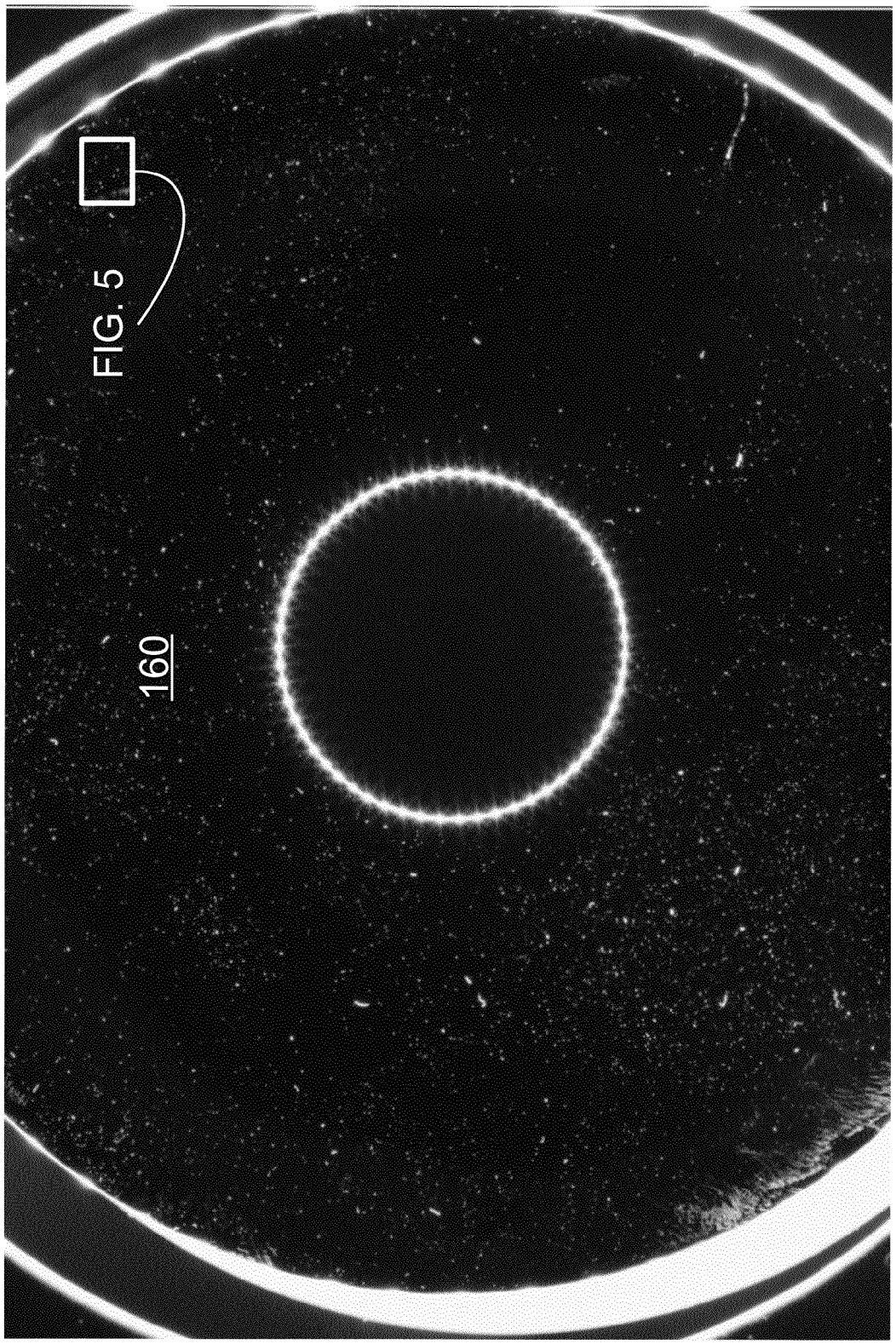

FIG. 4 provides an image of a map of surface features of an article in accordance with an embodiment.

FIG. 5 provides a close-up image of the map of surface features provided in FIG. 4 in accordance with an embodiment.

Figure 6B:
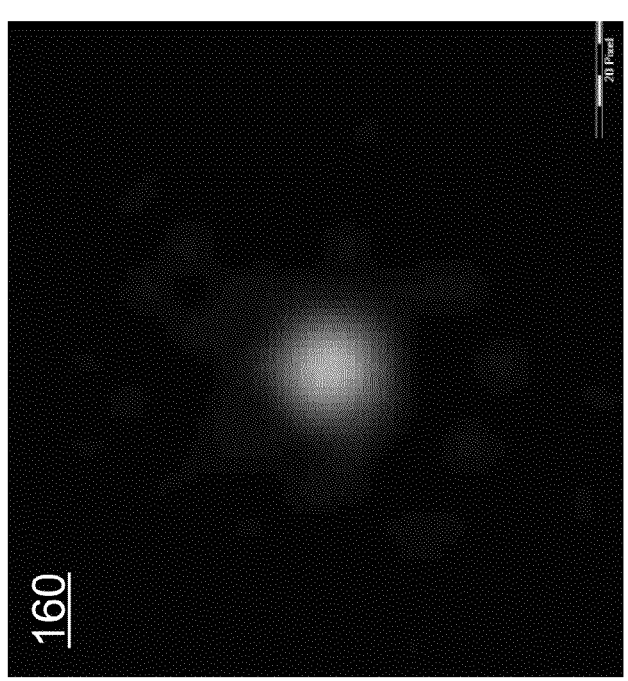
Figure 6A:
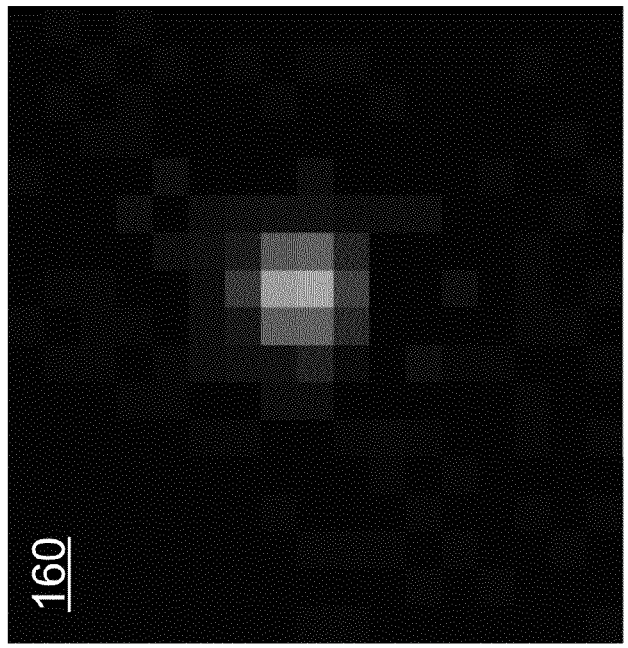

FIG. 6A (top) provides a close-up image of a surface feature from the map provided in FIG. 5, and FIG. 6A (bottom) provides photon scattering intensity distribution of the surface feature in accordance with an embodiment.

FIG. 6B (top) provides a pixel-interpolated image of the surface feature from FIG. 6A, and FIG. 6B (bottom) provides a pixel-interpolated photon scattering intensity distribution of the surface feature in accordance with an embodiment.

Figure 7:
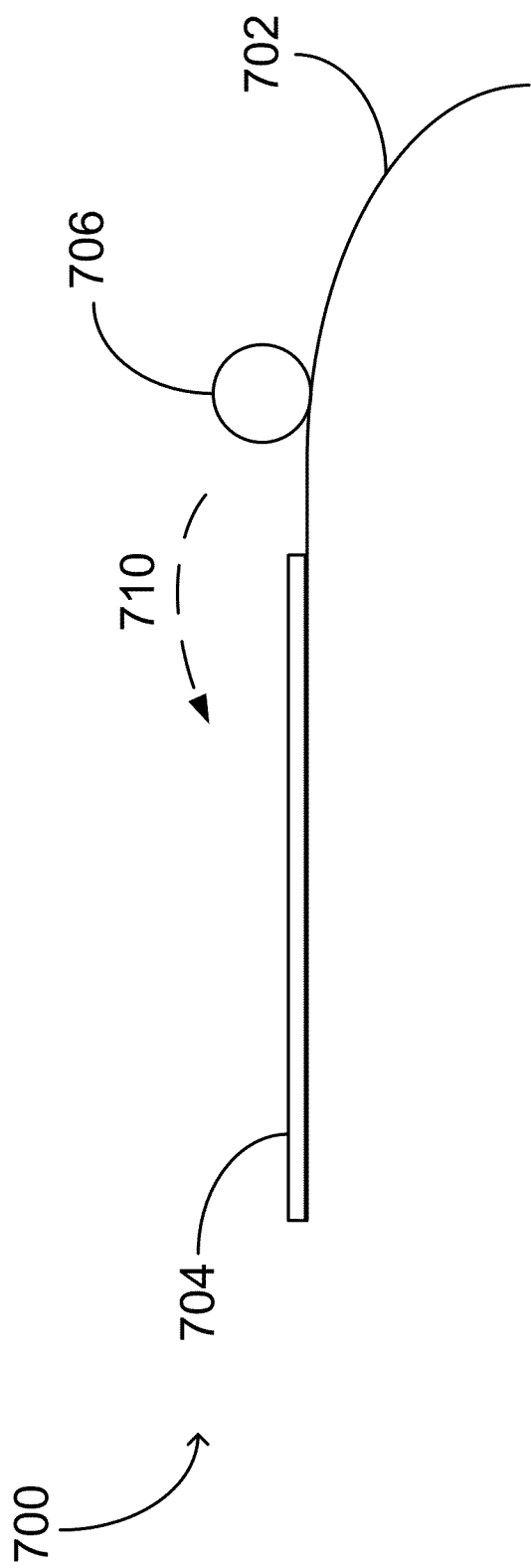

FIG. 7 provides a cross-sectional side view of an article having a feature on an edge of the article in accordance with an embodiment.

Figure 8:
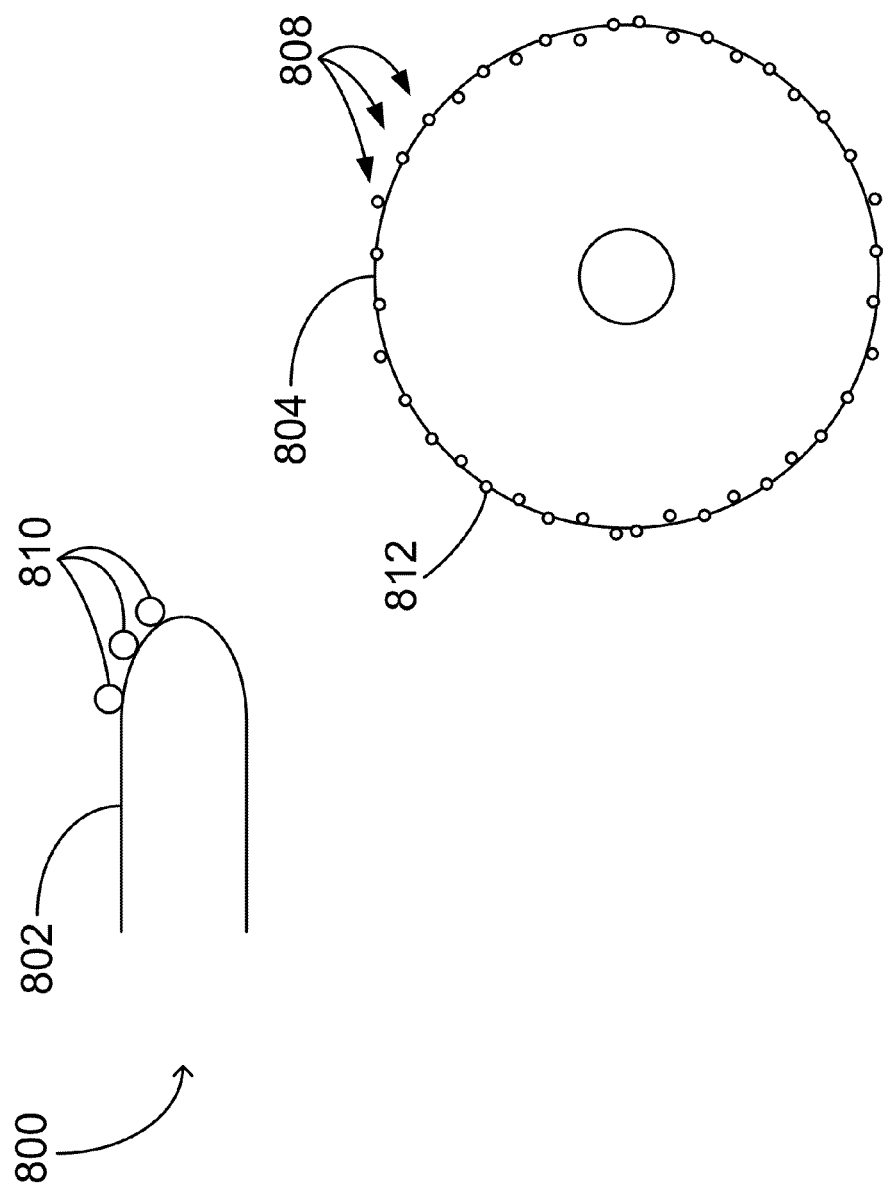

FIG. 8 provides a cross-sectional side view in combination with a plan view of an article having features on an edge of the article in accordance with an embodiment.

Figure 9:
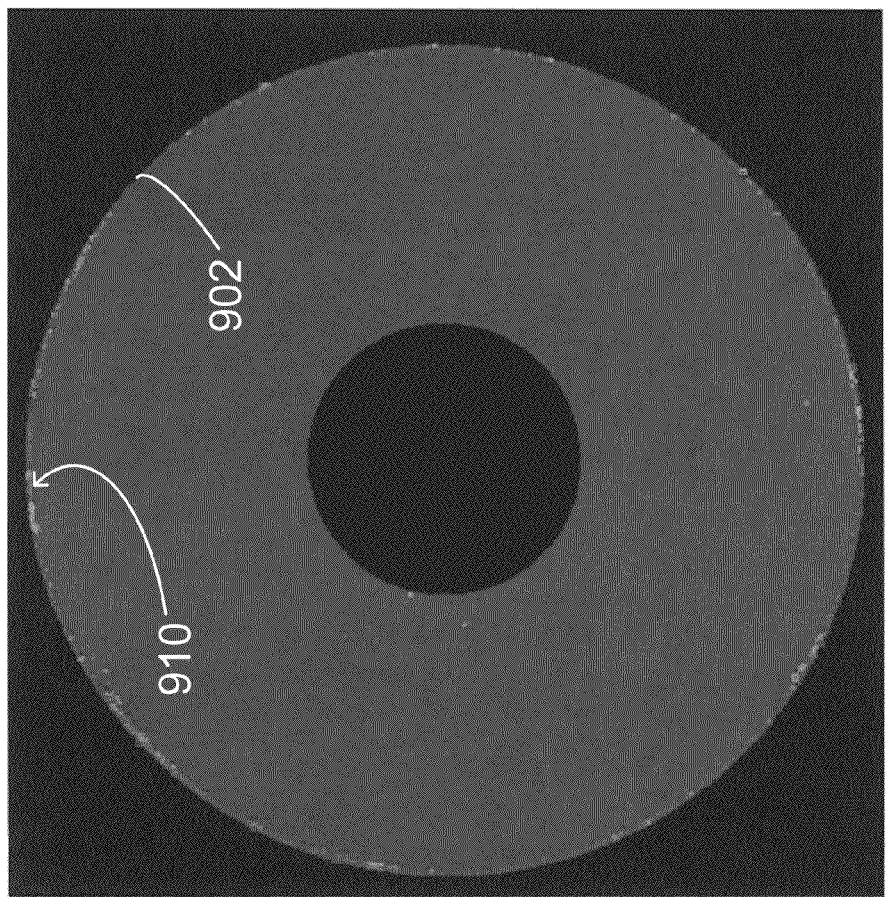

FIG. 9. provides an image of an article having defects in accordance with an embodiment.

Figure 10:
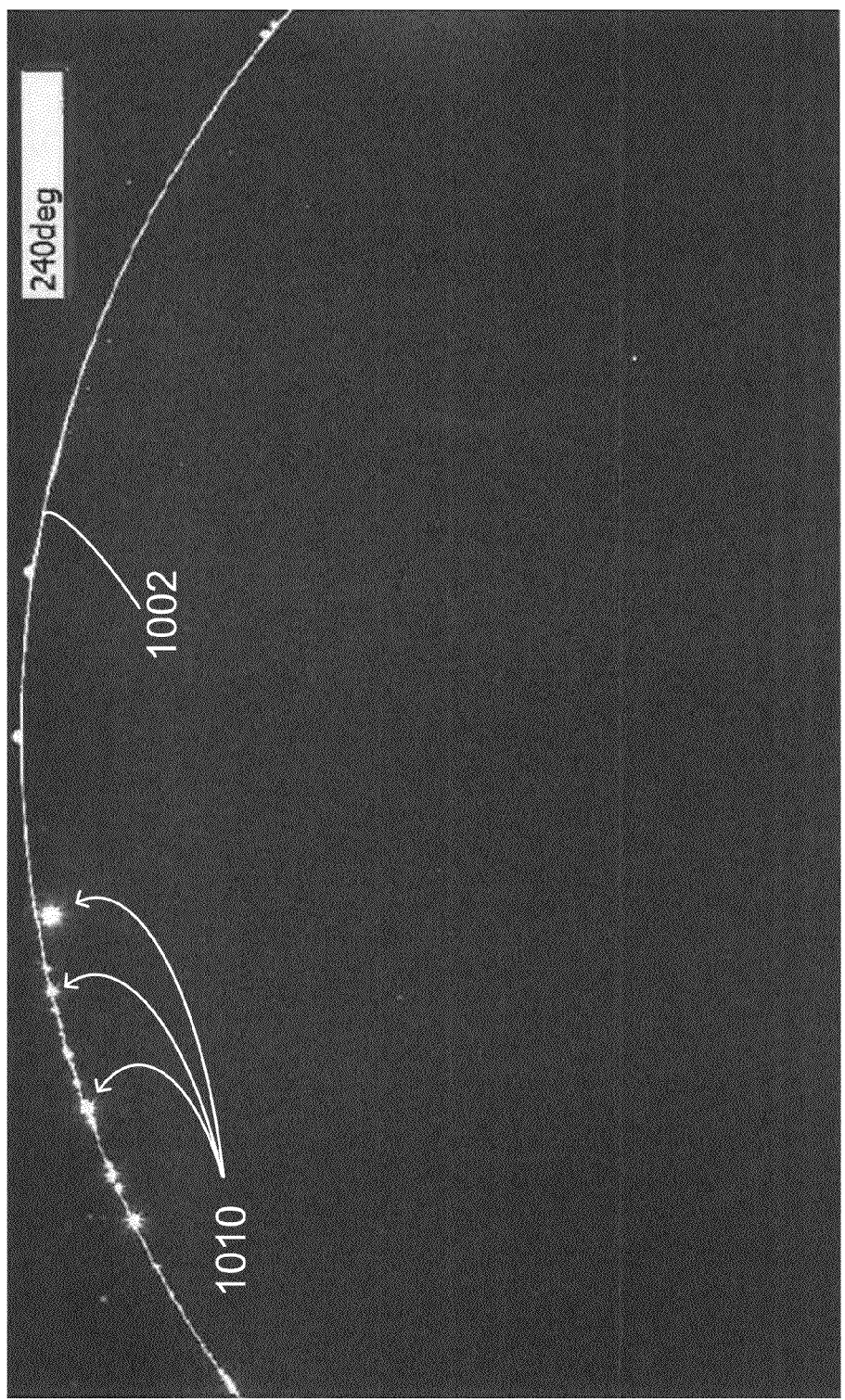

FIG. 10. provides an image of an article having one or more particles near the edge in accordance with an embodiment.

DESCRIPTION

Before particular embodiments are described in greater detail, it should be understood by persons having ordinary skill in the art that the concepts presented herein are not limited to the particular embodiments described and/or illustrated herein, as elements in such embodiments may vary. It should likewise be understood that a particular embodiment described and/or illustrated herein has elements which may be readily separated from the particular embodiment and optionally combined with any of several other embodiments or substituted for elements in any of several other embodiments described herein.

It should also be understood by persons having ordinary skill in the art that the terminology used herein is for the purpose of describing particular embodiments, and the terminology is not intended to be limiting. Unless indicated otherwise, ordinal numbers (e.g., first, second, third, etc.) are used to distinguish or identify different elements or steps in a group of elements or steps, and do not supply a serial or numerical limitation on the elements or steps. For example, "first," "second," and "third" elements or steps need not necessarily appear in that order, and the elements or steps need not necessarily be limited to three elements or steps. It should also be understood that, unless indicated otherwise, any labels such as "left," "right," "front," "back," "top," "bottom," "forward," "reverse," "clockwise," "counter clockwise," "up," "down," or other similar terms such as "upper," "lower," "aft," "fore," "vertical," "horizontal," "proximal," "distal," and the like are used for convenience and are not intended to imply, for example, any particular fixed location, orientation, or direction. Instead, such labels are used to reflect, for example, relative location, orientation, or directions. It should also be understood that the singular forms of "a," "an," and "the" include plural references unless the context clearly dictates otherwise.

Unless defined otherwise, all technical and scientific terms used herein have the same meaning as commonly understood by persons of ordinary skill in the art.

An article fabricated on a production line may be inspected for certain features, including defects that might degrade the performance of the article or a system comprising the article. For example, a hard disk for a hard disk drive may be fabricated on a production line and inspected for certain surface features, including surface and subsurface defects that might degrade the performance of the disk or the hard disk drive. Provided herein are apparatuses and methods for inspecting articles to detect and/or map certain surface features such as surface and/or subsurface defects. Particular embodiments will now be described in greater detail.

With respect to articles that may be inspected with apparatuses and methods herein, such articles include any article of manufacture or a workpiece thereof in any stage of manufacture having one or more optically smooth surfaces, examples of which include, but are not limited to, semiconductor wafers, magnetic recording media (e.g., hard disks for hard disk drives), and workpieces thereof in any stage of manufacture, including substrates or blanks made of transparent materials such as glass (e.g., glass substrates or glass blanks), quartz, polymers, or the like. Such articles may be inspected for certain features, including surface and/or subsurface defects that might degrade the performance of the article, which surface and/or subsurface defects include particle and stain contamination, as well as defects including scratches and voids. With respect to particle contamination, for example, particles trapped on a surface of an intermediate hard disk (i.e., workpiece) for a hard disk drive may damage subsequently sputtered films. Particle contamination may also contaminate a finished surface of a hard disk drive, leading to scratch formation, debris generation, and corruption of the spacing between the hard disk and the read-write head. As such, it is important to inspect articles with apparatus and methods herein to correct manufacturing trends leading to surface and/or subsurface defects and to increase product quality.

With respect to magnetic recording media (e.g., hard disks for hard disk drives) and workpieces thereof, particles and defects can be increasingly problematic as the head to media gap is reduced (e.g., approaches 1-2 nm). A magnetic recording medium such as a hard disk may be made by stamping or cutting the disk out of a material (e.g., glass, aluminum, or ceramic materials) and then polishing (e.g., surface polishing) the disk. This polishing may result in particles being moved from the area being polished to either one (or both) of an inner or outer edge of the disk such as an inner circumference or an outer circumference of the disk, respectively, either one (or both) of which inner or outer edge of the disk may be beveled, chamfered, or rounded. During the subsequent manufacture (e.g., sputtering processes) of the disk, or during operation of a device (e.g., hard disk drive) comprising one or more disks, these particles may subsequently be moved from the edge of the disk and deposited at or on the polished area. The particles may then become a contamination risk to the portions of the disk used for data storage, which portions of the disk used for disk storage may be coincident with the polished area.

The apparatus provided herein, unlike previous apparatuses, is operable to detect features (e.g., particles) on one or more edges of an article (e.g., magnetic recording medium such as a hard disk) such as one or more inner edges (e.g., an inner circumference of a hard disk) or outer edges (e.g., an outer circumference of a hard disk) of the article, which inner or outer edges of the article may be individually beveled, chamfered, or rounded. Further, tests and inspections done with magnetic heads flying above articles such as hard disks of hard disk drives do not reach the edges of the disks where particles may reside that could cause future contamination of the polished area and/or data storage area. Various embodiments are configured to detect particles and defects that may be located at the outer diameter of an article (e.g., a disk in areas where magnetic heads do not fly above). The particles and defects may be located and counted via an optical detection system disclosed herein. In some embodiments, light (e.g., monochromatic light) at reduced intensity (e.g., 20% intensity relative to polished surface imaging) is used at the edge of the article to provide sufficient flux for photon scattering from particles about the edge of the article. Image processing may then be used to determine the location and/or size (e.g., from photon scattering intensity distribution) for each particle or defect to be known. Various embodiments are configured to use high and/or low incidence angle light sources.

FIG. 1 provides a schematic for detection and/or mapping of surface features of articles, illustrating an apparatus 100 comprising a photon emitter 110, an optical setup 120, a photon detector array 130, and a mapping means 140, as well as an article 150 and a surface features map 160 of a surface of the article 150 in accordance with an embodiment; however, the articles and apparatuses described herein, as well as methods, are not limited to the embodiments in FIG. 1, as additional embodiments may be realized by the features described in more detail herein.

An apparatus for detection and/or mapping of surface features of articles may comprise a single photon emitter (e.g., see photon emitter 110 of FIG. 1) or a plurality of photon emitters, which may be used to emit photons onto a surface of an article, such as the entire surface of the article or some predetermined portion of the surface of the article (e.g., for gradational rotation of the article for piecewise inspection, if desired). In some embodiments, for example, the plurality of photon emitters may comprise at least 2, 3, 4, 5, 6, 7, 8, 9, or 10 photon emitters. In some embodiments, for example, the plurality of photon emitters may comprise no more than 10, 9, 8, 7, 6, 5, 4, 3, or 2 photon emitters. Combinations of the foregoing may also be used to describe the plurality of photon emitters. In some embodiments, for example, the plurality of photon emitters may comprise at least 2 photon emitters and no more than 10 photon emitters (e.g., between 2 and 10 photon emitters), such as at least 2 photon emitters and no more than 5 photon emitters (e.g., between 2 and 5 photon emitters). Further with respect to the plurality of photon emitters, each photon emitter of the plurality of photon emitters may be the same or different, or some combination thereof (e.g., at least 2 of the same photon emitter, with the remainder of photon emitters being different; at least 3 of the same photon emitter, with the remainder of photon emitters being different; etc.).

Whether the apparatus comprises a single photon emitter or a plurality of photon emitters, each photon emitter may emit photons onto a surface of an article at a distance and/or an angle optimized for one or more types of features, which types of features are described in more detail herein. The angle optimized for one or more types of features may be equal to the glancing angle, which glancing angle is the complement of the angle of incidence, and which angle of incidence is the angle between a ray comprising the emitted photons incident on the surface of the article and the normal (i.e., a line perpendicular to the surface of the article) at the point at which the ray is incident. The glancing angle may also be described as the angle between a ray comprising the emitted photons incident on the surface of the article and the surface at the point at which the ray is incident.

FIG. 2 provides a number of rays comprising emitted photons incident on a surface 152 of an article 150 that form a glancing angle with the surface 152. FIG. 2 further provides a number of rays comprising reflected photons that form an angle of reflection with the normal to the surface, which angle of reflection is equal to the angle of incidence, as well as a number of rays comprising scattered photons from a feature 154 on the surface 152 of the article 150, which rays comprising scattered photons form various scatter angles. A photon emitter may emit photons at a glancing angle ranging from 0° to 90°, wherein a glancing angle of 0° represents the photon emitter emitting photons onto the surface of the article from a side of the article, and wherein a glancing angle of 90° represents the photon emitter emitting photons onto the surface of the article from directly above the article. In some embodiments, for example, a photon emitter may emit photons onto a surface of an article such that the glancing angle is at least 0°, 5°, 10°, 15°, 20°, 25°, 30°, 35°, 40°, 45°, 50°, 55°, 60°, 65°, 70°, 75°, 80°, 85°, or 90°. In some embodiments, for example, a photon emitter may emit photons onto a surface of an article such that the glancing angle is no more than 90°, 85°, 80°, 75°, 70°, 65°, 60°, 55°, 50°, 45°, 40°, 35°, 30°, 25°, 20°, 15°, 10°, 5°, or 0°. Combinations of the foregoing may also be used to describe the glancing angle at which a photon emitter may emit photons onto a surface of an article. In some embodiments, for example, a photon emitter may emit photons onto a surface of an article such that the glancing angle is at least a 0° and no more than 90° (i.e., between 0° and 90°), such as least 0° and no more than 45° (i.e., between 0° and 45°), including at least 45° and no more than 90° (i.e., between 45° and 90°).

A photon emitter, optionally in combination with one or more additional photon emitters, and further optionally in combination with one or more additional photon emitters of the same type, may emit photons onto a surface of an article, such as the entire surface or some predetermined portion of the surface (e.g., for gradational rotation of the article for piecewise inspection, if desired). The photon emitter, optionally in combination with the one or more additional photon emitters, and further optionally in combination with the one or more additional photon emitters of the same type, may further emit photons onto the entire surface of the article or some predetermined portion of the surface such that the entire surface or the predetermined portion of the surface is uniformly or homogenously illuminated. With respect to transparent articles comprising materials such as glass, quartz, polymers, or the like, an optically smooth and/or reflective surface such as a mirror may be positioned under the transparent article to effect uniform or homogeneous illumination of the transparent article. Alternatively, the transparent article, which transparent article may have a first index of refraction, may be positioned in a medium (e.g., a gas such as air) having a second index of refraction, and one or more photon emitters may positioned or angled to emit photons into an edge of the transparent article to uniformly or homogeneously illuminate the transparent article by total internal reflection in accordance with Snell's law. Uniformly illuminating the entire surface of the article or some predetermined portion of the surface includes, but is not limited to, subjecting the entire surface of the article or some predetermined portion of the surface of the article to the same or about the same photon energy per unit time (e.g., photon power or photon flux) and/or photon power per unit area (e.g., photon flux density). In radiometric terms, uniformly illuminating includes, but is not limited to, subjecting the entire surface of the article or some predetermined portion of the surface of the article to the same or about the same radiant energy per unit time (e.g., radiant power or radiant flux) and/or radiant power per unit area (e.g., irradiance or radiant flux density).

With the appreciation that photons are the elementary particles of electromagnetic radiation or light, a photon emitter or light source may provide light comprising a relatively wide range of wavelengths (e.g., ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light comprising a relatively wide range of frequencies (e.g., ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. As discussed herein, a photon emitter or light source may be used in conjunction with one or more optical components of an optical setup to provide light having any of the foregoing qualities.

A photon emitter (or light source) may emit photons (or provide light) onto an article, such as onto an entire surface of the article, optionally including one or more edges of the article, some predetermined portion of the surface of the article, optionally including one or more edges of the article, one or more edges of the article, some predetermined portion of one or more edges of the article, etc. Photons (or light) having any one or more of the foregoing qualities (e.g., wavelength, frequency, polarization, coherence, etc.) may be emitted onto (provided to) the article at a power (e.g., irradiance or radiant flux density) suitable for a desired analysis. In some embodiments, for example, light is provided to the entire surface of the article or some predetermined portion thereof at an irradiance of at least 50, 100, 150, 200, 250, 300, 350, 400, 450, 500, 550, or 600 mW/cm2 for analysis of certain features, including surface and/or subsurface defects, which surface and/or subsurface defects include particle and stain contamination, as well as defects including scratches and voids. To effect analysis of one or more edges of the article, light may be provided to the article at a lower irradiance, wherein the lower irradiance is at least about 5%, 10%, 15%, 20%, 25%, 30%, 35%, 40%, 45%, or 50% lower than the irradiance for analysis of surface and/or subsurface defects. In some embodiments, for example, light is provided to the article or some predetermined portion thereof at an irradiance of at least 10, 20, 30, 40, 50, 60, 70, 80, 90, 100, 110, or 120 mW/cm2 for analysis of one or more edges of the article, including analysis of the one or more edges of the article for particle contamination.

In view of the foregoing, a photon emitter or light source may comprise a lamp such as a flash lamp, including a high-speed flash lamp, configured to minimize vibration while detecting photons scattered from features in a surface of an article with a photon detector array. In some embodiments, for example, a photon emitter or light source may comprise a high-speed Xe flash lamp such as a 500 W Xe flash lamp to minimize vibration while detecting photons scattered from features in a surface of an article with a photon detector array.

Also in view of the foregoing, a photon emitter or light source may comprise a collimated light source such as a laser, including a combination of lasers, configured to emit photons onto a surface of an article at one or more angles. In some embodiments, for example, a combination of lasers may be provided to a laser beam shaper such that the combination of lasers emits photons onto a surface of an article at one angle. In some embodiments, for example, a combination of lasers may be provided to a laser beam shaper such that the combination of lasers emits photons onto a surface of an article at multiple angles. In some embodiments, for example, at least 2, 4, 6, 8, 10, 12, 14, 16, 18, 20, 22, 24, 26, 28, or 30 lasers (or more) may be provided to a laser beam shaper such that the combination of lasers emits photons onto a surface of an article at one or more angles. In some embodiments, for example, no more than 30, 28, 26, 24, 22, 20, 18, 16, 14, 12, 10, 8, 6, 4, or 2 lasers may be provided to a laser beam shaper such that the combination of lasers emits photons onto a surface of an article at one or more angles. Combinations of the foregoing may also be used to describe combinations of lasers provided to a laser beam shaper. In some embodiments, for example, at least 2 lasers and no more than 30 lasers (e.g., between 2 and 30 lasers), such as at least 10 lasers and no more than 30 lasers (e.g., between 10 and 30 lasers), including at least 20 lasers and no more than 30 lasers (e.g., between 20 and 30 lasers), and further including at least 24 lasers and no more than 28 lasers (e.g., between 24 and 28 lasers) may be provided to a laser beam shaper such that the combination of lasers emits photons onto a surface of an article of an article at one or more angles.

Further in view of the foregoing, a photon emitter or light source may comprise a two-dimensional light source such as a combination of point light sources, including a linear combination, an arcuate combination, etc. of point light sources configured to emit photons onto a surface of an article. In some embodiments, for example, a two-dimensional light source may comprise a combination of at least 10, 20, 40, 60, 80, 100, 110, 120, 140, 160, 180, or 200 (or more) point light sources. In some embodiments, for example, a two-dimensional light source may comprise a combination of no more than 200, 180, 160, 140, 120, 100, 80, 60, 40, 20, or 10 point light sources. Combinations of the foregoing may also be used to describe two-dimensional light sources comprising combinations of point light sources. In some embodiments, for example, a two-dimensional light source may comprise a combination of at least 10 and no more than 200 (e.g., between 10 and 200) point light sources, such as at least 40 and no more than 160 (e.g., between 40 and 160) point light sources, including at least 60 and no more than 140 (e.g., between 60 and 140) point light sources, and further including at least 80 and no more than 120 (e.g., between 80 and 120) point light sources. Such point light sources may be linearly combined to form a two-dimensional light source such as a strip light. Such point light sources may be arcuately combined to form a two-dimensional light source such as a ring light. In some embodiments, for example, a photon emitter or light source may comprise a two-dimensional light source comprising at least 60 point light sources, such as a ring light comprising at least 60 point light sources, including a ring light comprising at least 60 light-emitting diodes ("LEDs"), and further including a ring light comprising at least 100 LEDs. A two-dimensional light source comprising LEDs may comprise white LEDs, wherein each LED has a power of at least 10 mW. An LED-based ring light may enhance features such as scratches (e.g., circumferential scratches) and/or voids in surfaces of articles, especially when the LED-based ring light is configured to emit photons onto the surfaces of the articles with lower angles (e.g., glancing angle equal to or less than 45°).

An apparatus for detection and/or mapping of surface features of articles may further comprise an optical setup (e.g., see optical setup 120 of FIG. 1), which optical setup may manipulate photons emitted from one or more photon emitters and/or photons scattered from surface features of articles. With the appreciation that photons are the elementary particles of electromagnetic radiation or light, the optical setup may manipulate light emitted from one or more photon emitters and/or light scattered from surface features of articles. The optical setup up may comprise any of a number of optical components placed in the optical path before an article such that the optical components may be used to manipulate photons/light emitted from one or more photon emitters before uniformly or homogenously illuminating the entire surface or the predetermined portion of the surface of the article. The optical setup up may comprise any of a number of optical components placed in the optical path after an article such that the optical components may be used to manipulate photons/light scattered from features in a surface of the article. The forgoing optical components may include, but are not limited to, optical components such as lenses, mirrors, and filters. With respect to optical components such as filters, such filters may include, for example, wave filters and polarization filters. Wave filters may be used in conjunction with photon emitters described herein to provide light comprising a relatively wide range of wavelengths/frequencies, a relatively narrow range of wavelengths/frequencies, or a particular wavelength/frequency. Polarization filters may be used in conjunction with photon emitters described herein to provide light of a desired polarization including polarized light, partially polarized light, or nonpolarized light.

An optical setup for an apparatus for detection and/or mapping of surface features of articles may comprise a single lens or a plurality of lenses, including, but not limited to, a combination of a lens coupled to a photon detector array (e.g., photon detector array 130 of FIG. 1) for collecting and detecting photons scattered from features in a surface of an article. The lens coupled to the photon detector array may be an objective lens, such as a telecentric lens, including an object-space telecentric lens (i.e., entrance pupil at infinity), an image-space telecentric lens (i.e., exit pupil at infinity), or a double telecentric lens (i.e., both pupils at infinity). Coupling a telecentric lens to a photon detector array reduces errors with respect to the mapped position of surface features of articles, reduces distortion of surface features of articles, and/or enables quantitative analysis of photons scattered from surface features of articles, which quantitative analysis includes integration of photon scattering intensity distribution for size determination of surface features of articles.

To detect photons scattered from surface features of articles, an apparatus for detection and/or mapping of surface features of articles may further comprise a single photon detector array (e.g., see photon detector array 130 of FIG. 1) comprising a plurality of photon detectors or a plurality of photon detector arrays, each comprising a plurality of photon detectors. In some embodiments, for example, the plurality of photon detector arrays may comprise at least 2, 3, 4, 5, 6, 7, 8, 9, or photon detector arrays. In some embodiments, for example, the plurality of photon detector arrays may comprise no more than 10, 9, 8, 7, 6, 5, 4, 3, or 2 photon detector arrays. Combinations of the foregoing may also be used to describe the plurality of photon detector arrays. In some embodiments, for example, the plurality of photon detector arrays may comprise at least 2 photon detector arrays and no more than 10 photon detector arrays (e.g., between 2 and 10 photon detector arrays), such as at least 2 photon detector arrays and no more than 5 photon detector arrays (e.g., between 2 and 5 photon detector arrays). Further with respect to the plurality of photon detector arrays, each photon detector array of the plurality of photon detector arrays may be the same or different, or some combination thereof (e.g., at least 2 of the same photon detector array, with the remainder of photon detector arrays being different; at least 3 of the same photon detector array, with the remainder of photon detector arrays being different; etc.).

Whether the apparatus comprises a single photon detector array or a plurality of photon detector arrays, each photon detector array may be oriented to detect photons scattered from surface features of an article at an optimized distance and/or an optimized angle for a maximum acceptance of scattered light and/or one or more types of features, which types of features are described in more detail herein. Likewise, a photon detector array and lens (e.g., telecentric lens) combination may be oriented to collect and detect photons scattered from surface features of an article at an optimized distance and/or an optimized angle for a maximum acceptance of scattered light and/or one or more types of features. Such an optimized angle may be the angle between a ray comprising the center line axis of the photon detector array and/or the lens extended to the surface of the article and the normal (i.e., a line perpendicular to the surface of the article) at the point at which the ray is extended. The optimized angle may be equal to or otherwise include a scatter angle for one or more types of features, and the scatter angle may be a different angle than the angle of reflection, which angle of reflection is equal to the angle of incidence as described herein. FIG. 2 provides a number of rays comprising scattered photons from a feature 154 on a surface 152 of an article 150 that form various scatter angles, as well as a number of rays comprising reflected photons that form an angle of reflection with the normal to the surface. A photon detector array or photon detector array and lens combination may be oriented at an optimized angle ranging from 0° to 90°, wherein an optimized angle of 0° represents orientation of the photon detector array or the photon detector array and lens combination at a side of the article, and wherein an optimized angle of 90° represents orientation of the photon detector array or photon detector array and lens combination directly above the article. In some embodiments, for example, a photon detector array or photon detector array and lens combination may be oriented at an optimized angle of at least 0°, 5°, 10°, 15°, 20°, 25°, 30°, 35°, 40°, 45°, 50°, 55°, 60°, 65°, 70°, 75°, 80°, 85°, or 90°. In some embodiments, for example, a photon detector array or photon detector array and lens combination may be oriented at an optimized angle of no more than 90°, 85°, 80°, 75°, 70°, 65°, 60°, 55°, 50°, 45°, 40°, 35°, 30°, 25°, 20°, 15°, 10°, or 5°. Combinations of the foregoing may also be used to describe the optimized angle at which the photon detector array or photon detector array and lens combination may be oriented. In some embodiments, for example, a photon detector array or photon detector array and lens combination may be oriented at an optimized angle of at least a 0° and no more than a 90° (i.e., between 0° and 90°), such as least 0° and no more than 45° (i.e., between 0° and 45°), including at least 45° and no more than 90° (i.e., between 45° and 90°).

A photon detector array, optionally in combination with a lens (e.g., telecentric lens), and further optionally in combination with one or more additional photon detector arrays or photon-detector-array-and-lens combinations, and even further optionally in combination with one or more additional photon detector arrays or photon-detector-array-and-lens combinations of the same type, may detect photons scattered from features in a surface of an article, such as the entire surface of the article or some predetermined portion of the surface of the article. The photon detector array, optionally in combination with a lens (e.g., telecentric lens), and further optionally in combination with one or more additional photon detector arrays or photon-detector-array-and-lens combinations, and even further optionally in combination with one or more additional photon detector arrays or photon-detector-array-and-lens combinations of the same type, may detect photons scattered from features in a surface of an article, such as the entire surface of the article or some predetermined portion of the surface of the article, while oriented at a distance and/or an angle optimized for a maximum acceptance of scattered light and/or one or more types of features. As provided herein, the angle optimized for one or more types of features may be equal to or otherwise include a scatter angle for one or more types of features.

With the appreciation that photons are the elementary particles of electromagnetic radiation or light, a photon detector array or light detector array may detect light comprising a relatively wide range of wavelengths (e.g., ultraviolet-visible, visible, infrared, etc.), a relatively narrow range of wavelengths (e.g., a subdivision of ultraviolet such as UVA, UVB, UVC, etc.; a subdivision of visible such as red, green, blue, etc.; a subdivision of infrared such as near infrared, mid-infrared; etc.), or a particular wavelength (e.g., monochromatic); light comprising a relatively wide range of frequencies (e.g., ultraviolet-visible, visible, infrared, etc.), a relatively narrow range of frequencies (e.g., a subdivision of ultraviolet such as UVA, UVB, UVC, etc.; a subdivision of visible such as red, green, blue, etc.; a subdivision of infrared such as near infrared, mid-infrared; etc.), or a particular frequency (e.g., monochromatic); polarized (e.g., linear polarization, circular polarization, etc.) light, partially polarized light, or nonpolarized light; and/or light with different degrees of temporal and/or spatial coherence ranging from coherent light (e.g., laser) to noncoherent light. As discussed herein, a photon detector array or light detector array may be used in conjunction with one or more optical components of an optical setup to detect light having any of the foregoing qualities.

A photon detector array may comprise a plurality of pixel sensors, which pixel sensors, in turn, may each comprise a photon detector (e.g., a photodiode) coupled to a circuit comprising a transistor configured for amplification. Features of a photon detector array comprising such pixel sensors include, but are not limited to, low temperature operation (e.g., down to −40° C.), low electron noise (e.g., 2-10 e-RMS; 1 e-RMS; <1 e-RMS; etc.), wide dynamic range (e.g., 30,000:1, 8,500:1; 3,000:1; etc.), and/or decreased photon/light collection time. A photon detector array may comprise a large number of pixel sensors (e.g., 1,000,000 or 1M pixel sensors) arranged in rows and columns of a two-dimensional array, wherein each pixel sensor comprises a photon detector coupled to an amplifier. In some embodiments, for example, a photon detector array may comprise at least 1M, 2M, 3M, 4M, 5M, 6M, 7M, 8M, 9M, 10M, or more, pixel sensors arranged in rows and columns of a two-dimensional array. In some embodiments, for example, a photon detector array may comprise no more than 10M, 9M, 8M, 7M, 6M, 5M, 4M, 3M, 2M, 1M, pixel sensors arranged in rows and columns of a two-dimensional array. Combinations of the foregoing may also be used to describe the number of pixel sensors in a photon detector array. In some embodiments, for example, a photon detector array may comprise at least 1M and no more than 10M (e.g., between 1M and 10M) pixel sensors arranged in rows and columns of a two-dimensional array, such as at least 1M and no more than 8M (e.g., between 1M and 8M) pixel sensors, including at least 1M and no more than 6M (e.g., between 1M and 8M) pixel sensors, further including at least 2M and no more than 6M (e.g., between 1M and 8M) pixel sensors, and even further including at least 2M and no more than 5M (e.g., between 2M and 5M) pixel sensors.

Due to surface reflections of surface features in articles and/or small angle scattering (e.g., 4π scattering), surface features may appear much larger in size enabling pixel sensors larger the than surface features to be used. In some embodiments, for example, a photon detector array may comprise micrometer-sized (i.e., admits of μm units as measured) pixel sensors at least 1 μm, 2 μm, 3 μm, 4 μm, 5 μm, 6 μm, 7 μm, 8 μm, 9 μm, or 10 μm in their smallest dimension. In some embodiments, for example, a photon detector array may comprise micrometer-sized pixel sensors no more than 10 μm, 9 μm, 8 μm, 7 μm, 6 μm, 5 μm, 4 μm, 3 μm, 2 μm, or 1 μm in their smallest dimension. Combinations of the foregoing may also be used to describe dimensions of micrometer-sized pixel sensors in photon detector arrays. In some embodiments, for example, a photon detector array may comprise micrometer-sized pixel sensors at least 1 μm and no more than 10 μm (e.g., between 1 μm and 10 μm) in their smallest dimension, such as at least 1 μm and no more than 7 μm (e.g., between 1 μm and 7 μm), including at least 4 μm and no more than 10 μm (e.g., between 4 μm and 10 μm), and further including at least 4 μm and no more than 7 μm (e.g., between 4 μm and 7 μm). Such micrometer-sized pixel sensors may be used in the apparatus to detect and/or map surface features of articles that are more than 100 times smaller than the micrometer-sized pixel sensors.

In view of the foregoing, the single photon detector array or the plurality of photon detector arrays may each comprise a complementary metal-oxide semiconductor ("CMOS") or a scientific complementary metal-oxide semiconductor ("sCMOS"), each of which may optionally be part of CMOS camera or a sCMOS camera, respectively. Alternatively, the single photon detector array or the plurality of photon detector arrays may each comprise a charge-coupled device ("CCD"), which may optionally be part of CCD camera. While a CCD-based photon detector array might have a slower recording speed than a CMOS-based or sCMOS-based photon detector array, a CCD-based photon detector array may be desirable in certain applications requiring less electronic and/or image noise. Furthermore, a plurality of photon detector arrays is not limited to combinations of either CMOS/sCMOS-based photon detector arrays or CCD-based photon-detector arrays, as a plurality of photon detector arrays may comprise a combination of any of a number of CMOS/sCMOS-based photon detector arrays and CCD-based photon-detector arrays in certain applications that benefit from employing each type of technology.

FIG. 3 provides a schematic for detection of surface features in an article, illustrating a close-up, cross-sectional view of an apparatus comprising an optical setup and a photon detector array. As shown, article 150 comprises a surface 152 and at least surface feature 154. Photons emitted from a single photon emitter or a plurality of photon emitters may be scattered by the surface feature 154 and collected and detected by a combination comprising an optical setup 120 coupled to a photon detector array 130, which combination may be place at an optimized distance and/or an optimized angle for a maximum acceptance of scattered photons and/or one or more types of features. The optical setup 120, which may comprise a telecentric lens, may collect and focus the photons scattered from the surface feature 154 onto one or more pixel sensors 132 of photon detector array 130, which one or more pixel sensors each comprises a photon detector coupled to an amplifier. The one or more pixel sensors 132, each of which corresponds to a pixel in a map of an article's surface features, may provide one or more signals to the mapping means for mapping the surface feature 154 as shown, for example, in FIG. 6A, which is a close-up image of the map of surface features provided in FIG. 5, which, in turn, is a close-up image of the map of surface features provided in FIG. 4. The mapping means may subsequently use pixel interpolation for further mapping the surface feature 154 as shown in FIG. 6B.

An apparatus for detection and/or mapping of surface features of articles may further comprise one or more computers or equivalent devices (e.g., devices that include primary and/or secondary memory and one or more processing elements operable to carry out arithmetic and logical operations) including, but not limited to, servers, workstations, desktop computers, nettops, laptops, netbooks, and mobile devices such as tablets and smartphones, which computers or equivalent devices may contain graphics processing units ("GPU"s), application-specific integrated circuits ("ASIC"s), field-programmable gate arrays ("FPGA"s), etc. The computers or equivalent devices may include a computer-readable storage medium for instructions making the apparatus operable to, but not limited to, convey each article to the apparatus for inspection; position each article for inspection, optionally including gradational rotation of the article for piecewise inspection; hold each article for inspection; insert optical components into the optical setup; remove optical components from the optical setup; position and/or otherwise adjust optical components for inspection; move each photon emitter into position for inspection, wherein the position for inspection may include an optimized photon emitter-article distance and/or angle (e.g., glancing angle); switch each photon emitter on and off, or otherwise between modes for emitting photons and not emitting photons; move each photon detector array into position for inspection, wherein the position for inspection may include an optimized photon detector array-article distance and/or angle (e.g., scatter angle); switch each photon detector array on and off, or otherwise between modes for detecting photons and not detecting photons; process photon detector array signals, optionally including pixel interpolation for better accuracy (e.g., 10× better than pixel size) with respect to the mapped position of surface features; map surface features of articles from photon detector array signals or processed photon detector array signals; characterize surface features of articles with respect to type (e.g., particle, stains, scratches, voids, etc.) and/or size (e.g., volume from integration of photon scattering intensity distribution); catalog surface features of articles; and determine trends with respect to surface features of articles.

The apparatus comprising the one or more computers or equivalent devices may be operable to detect and/or map surface features of articles that are nanometer-sized (i.e., admits of nm units as measured) or smaller in their smallest dimension (e.g., length, width, height, or depth, depending on the surface feature); however, the apparatus is not limited to mapping surface features of articles that are nanometer-sized or smaller, as the apparatus may be operable to map surface features of articles that are micrometer-sized (i.e., admits of μm units as measured) or larger. In some embodiments, for example, the apparatus comprising the one or more computers or equivalent devices may be operable to map surface features of articles smaller than 500 nm, 250 nm, 200 nm, 150 nm, 125 nm, 110 nm, 100 nm, 90 nm, 80 nm, 70 nm, 60 nm, 50 nm, 40 nm, 30 nm, 20 nm, 10 nm, or 1 nm (10 Å) in their smallest dimension, or even smaller, such as surface features of articles smaller than 9 Å, 8 Å, 7 Å, 6 Å, 5 Å, 4 Å, 3 Å, 2 Å, or 1 Å in their smallest dimension. In view of the foregoing, the apparatus comprising the one or more computers or equivalent devices may be operable to, in some embodiments, for example, map surface features of articles between 0.1 nm and 1000 nm, such as between 0.1 nm and 500 nm, including between 0.1 nm and 250 nm, and further including between 0.1 nm and 100 nm, and even further including between 0.1 nm and 80 nm.

In view of the foregoing, the apparatus may be operable to detect and/or map surface features of articles such as particle contamination comprising particles that are nanometer-sized (i.e., admits of nm units as measured) or smaller in their smallest dimension (e.g., length, width, or height). In some embodiments, for example, the apparatus may be operable to detect and/or map surface and/or subsurface particles smaller than 125 nm, such as smaller than 100 nm, including smaller than 80 nm, and further including smaller than 10 nm in their smallest dimension. In some embodiments, for example, the apparatus may be operable to map surface and/or subsurface particles smaller than 4 nm in height.

Further in view of the foregoing, the apparatus may be operable to detect and/or map surface features of articles such as defects comprising scratches (e.g., circumferential scratches) that are micrometer-sized (i.e., admits of μm units as measured) or smaller, such as nanometer-sized (i.e., admits of nm units as measured) or smaller, such as angstrom-sized (i.e., admits of Å units as measured) or smaller, in their smallest dimension (e.g., length, width, or depth). With respect to micrometer-sized scratches, the apparatus may be operable to detect and/or map scratches from, for example, 1 μm to 1000 μm in length, which may be significantly longer than the wavelength of photons/light emitted from a photon emitter of the apparatus. In some embodiments, for example, the apparatus may be operable to detect and/or map surface features such as defects comprising scratches smaller than 1000 μm, such as smaller than 500 μm, including smaller than 250 μm, further including smaller than 100 μm, and even further including smaller than 50 µm in scratch length. With respect to nanometer-sized scratches, the apparatus may be operable to detect and/or map scratches from, for example, 1 nm to 500 nm in scratch width. In some embodiments, for example, the apparatus may be operable to detect and/or map surface features such as defects comprising scratches smaller than 500 nm, such as smaller than 250 nm, including smaller than 100 nm, further including smaller than 50 nm, and even further including smaller than 15 nm in scratch width. Surprisingly, due to a high level of spatial coherence, the apparatus may be operable to detect and/or map angstrom-sized scratches with respect to scratch depth. In some embodiments, for example, the apparatus may be operable to detect and/or map surface features such as defects comprising scratches smaller than 50 Å, such as smaller than 25 Å, including smaller than 10 Å, further including smaller than 5 Å, and even further including smaller than 1 Å (e.g., 0.5 Å) in scratch depth. For example, the apparatus may be operable to detect and/or map surface features such as defects comprising scratches smaller than 500 µm in length, smaller than 100 nm in width, and smaller than 50 Å in depth.

The apparatus comprising the one or more computers or equivalent devices may be operable to accurately and/or precisely map the position of a feature on an article's surface. With respect to accuracy, the apparatus comprising the one or more computers or equivalent devices may be operable to map the position of a feature on an article's surface within a micrometer-sized (i.e., admits of µm units as measured) radius or better. In some embodiments, for example, the apparatus comprising the one or more computers or equivalent devices may be operable to accurately map the position of a feature on an article's surface within a radius of 100 µm, 90 µm, 80 µm, 70 µm, 60 µm, 50 µm, 40 µm, 30 µm, 20 µm, 10 µm, 9 µm, 8 µm, 7 µm, 6 µm, 5 µm, 4 µm, 3 µm, 2 µm, or 1 µm, or better. Combinations of the foregoing may also be used to describe the accuracy with which the apparatus comprising the one or more computers or equivalent devices may map the position of a feature on an article's surface. In some embodiments, for example, the apparatus comprising the one or more computers or equivalent devices may be operable to accurately map the position of a feature on an article's surface within a radius ranging from 1 µm to 100 µm, such as from 1 µm to 50 µm, including from 1 µm to 30 µm, and further including from 5 µm to 10 µm.

The apparatus comprising the one or more computers or equivalent devices may be operable to accurately and/or precisely map the position of a feature on an article's surface (e.g., FIGS. 6A (top) and 6B (top)) along with the feature's photon scattering intensity distribution (e.g., FIGS. 6A (bottom) and 6B (bottom)). Mathematical integration of such a photon scattering intensity distribution provides the size (e.g., volume) of the respective feature. As such, the apparatus described herein may characterize surface features both qualitatively and quantitatively. With respect to qualitative characterization of surface features, qualitative characterization includes a determination of surface feature type (e.g., particle, stain, scratch, void, etc.). With respect to quantitative characterization of surface features, quantitative characterization includes a determination of surface feature position on the article and/or surface feature size. Quantitative characterization of surface features may further include the total number of surface features per article, as well as the number of each type of surface feature. Such characterization information may be cataloged across a plurality of articles and be used to correct manufacturing trends leading to surface and/or subsurface defects.

Depending upon factors that may include the type of article, the type of surface features, and the like, it may be desirable at times to increase the number of photons (e.g., photon energy) emitted from a single photon emitter or a plurality of photon emitters to provide an increased scattering signal for characterization (e.g., qualitative and/or quantitative) of surface features of articles. Such an increase in photon energy may be with respect to unit time for increased photon power or photon flux, or with respect to unit area for increased photon flux density. Alternately, or in addition, it may be desirable to increase detection time of a single photon emitter or a plurality of photon emitters to detect more photons for accurately and/or precisely mapping surface features. Alternately to one or both of increasing the photon energy or detection time, or in addition to increasing the photon energy and detection time, it may be desirable at times to minimize background noise including stray light from one or more photon emitters, background light, and/or background fluorescent radiation.

The apparatus described herein may be configured to process or inspect articles at a rate greater than or commensurate with the rate at which the articles or workpieces thereof are produced. In some embodiments, for example, the apparatus may be configured to process or inspect articles at a rate of at least 1, 2, 3, 4, 5, 6, 7, 8, 9, 10, 12, 14, 16, 18, or 20 article(s) per second, which rate may be commensurate with the rate at which the articles or workpieces thereof are produced. In some embodiments, for example, the apparatus may be configured to process or inspect articles at a rate of no more than 20, 18, 16, 14, 12, 10, 9, 8, 7, 6, 5, 4, 3, 2, or 1 article(s) per second, which rate may be commensurate with the rate at which the articles or workpieces thereof are produced. Combinations of the foregoing may also be used to describe the rate at which the articles or workpieces thereof are processed or inspected by the apparatus. In some embodiments, for example, the apparatus may be configured to process or inspect at least 1 and no more than 20 articles per second (e.g., between 1 and 20 articles per second), such as at least 1 and no more than 10 articles per second (e.g., between 1 and 10 articles per second), including at least 1 and no more than 5 articles per second (e.g., between 1 and 5 articles per second). Processing or inspecting articles at rates greater than or commensurate with the rate at which the articles or workpieces thereof are produced is a function of many features of the apparatus described herein, including, but not limited to, photon emitters and/or articles that need not be moved (e.g., for scanning) during processing or inspecting. For example, an article such as a hard disk of a hard disk drive need not be rotated during processing or inspecting. As such, the apparatus may be configured to hold an article stationary while emitting photons onto the surface of the article.

While the apparatus may be configured to process or inspect articles a rate greater than or commensurate with the rate at which the articles or workpieces thereof are produced, the apparatus may operate at a slower rate if needed. In some embodiments, for example, the apparatus may be configured to process or inspect articles at a rate less than one article per second. In such embodiments, for example, the apparatus may be configured to process or inspect articles at a rate less than one article per 5, 10, 25, 50, 75, or 100, or more, second(s).

FIG. 7 provides a cross-sectional side view of an article having a feature on an edge of the article. In some embodiments, FIG. 7 depicts article 700 having a feature 706 on a surface edge of article 700. Feature 706 may be a particle or a defect.

Surface 702 includes polished area 704. In some embodiments, polished area 704 is configured for data storage. In various embodiments, feature 706 includes a particle that may have become positioned on surface 702 of article 700 during polishing (e.g., diamond polishing) of polished area 704. Feature 706 may also become positioned on surface 702 during shaping of article 700 (e.g., stamping or cutting of article 700).

Feature 706 may contaminate polished area 704 of article 700. For example, feature 706 may move onto polished area 704 as indicated by arrow 710 during processing, manufacturing, or during an operational state of article 700. Feature 706 may thereby interfere with reading of data stored in polished area 704.

FIG. 8 provides a cross-sectional side view in combination with a plan view of an article having features on an edge of the article. FIG. 8 depicts a side view of article 800 and a plan view of article 800 having features thereon. Article 800 has surface 802 which include features 810 located thereon. Features 810 may be located at surface edges of article 800. Features 810 may be particles or defects.

Article 800 has outer diameter edge 804 as shown in a plan view. Features 808 may be located at various locations around outer diameter edge 804. Features 810 may correspond to features 812 as depicted in the plan view.

Various embodiments are configured to detect features (e.g., particles and/or defects) that may be located at the outer diameter of an article (e.g., at the edge of a disk in areas where magnetic heads do not fly). In some embodiments, photon detector arrays (e.g., CMOS, sCMOS) larger than the article (e.g., disk) are used and thereby provide feature (e.g., particles and defect) detection at the edges of an article. In some embodiments, a telecentric lens larger than the article may also be used to collect photons to image the article. In some embodiments, for example, a combination of a telecentric lens and a photon detector array larger than the article may be used to image the article.

The particle contamination may be located and counted via an optical detection system (e.g., apparatus 100). In some embodiments, light (e.g., monochromatic light) at reduced intensity is used at the edge of the article to provide sufficient flux for photon scattering from particles about the edge of the article. Image processing may then be used to determine the location and/or size (e.g., from photon scattering intensity distribution) for each particle to be known. Various embodiments are configured to use high and/or low incidence angle light sources. In some embodiments, illumination intensity and/or exposure time can be adjusted to obtain multiple images at different illumination intensities. For example, dynamic exposure may be used to detect relatively small particles. Various embodiments may focus illumination selectively on an edge portion of the article. In some embodiments, different illumination angles may be used to vary the response thereby offering multiple degrees of freedom for tuning and optimizing, as described herein.

FIG. 9 provides an image of an article having particles and/or defects in accordance with an embodiment. In some embodiments, FIG. 9 depicts an image of a 65 mm disk with reduced illumination showing located particles and/or defects indicated by different (e.g., lighter) shades at the edge of the disk. Article 900 has outer diameter edge 902. Particles and/or defects on outer diameter edge 902 are illuminated as shown by dots 910 around outer diameter edge 902. In various embodiments, dots 910 correspond to light scattered by particles and/or defects around outer diameter edge 902. In various embodiments, particles and/or defects may be detected by changing the light intensity. In some embodiments, low intensity light (e.g., approximately 20% intensity relative to polished surface imaging) may be used to detect features at the edges of an article.

FIG. 10 provides an image of an article having one or more particles near the edge in accordance with an embodiment. In some embodiments, FIG. 10 depicts an image of a 95 mm edge inspection showing one segment of circumference. Particles show up as round scatter points super-imposed on the disk edge. Article 1000 has outer diameter edge 1002. Particles on outer diameter edge 1002 are illuminated as shown by dots 1010 around outer diameter edge 1002. In various embodiments, dots 1010 correspond to light scattered by particles around outer diameter edge 1002.

In various embodiments, lower intensity light impinging on the edge of the article (e.g., disk) reveals point scatters from defects and/or particles. The morphology of the particle/defect may then be used to determine whether the scattering of light was due to a particle or a defect.

As such, as provided herein, is an apparatus, including a photon emitter configured to emit photons onto a surface of an article and configured to emit photons onto surface edges of the article, a photon detector array including a plurality of photon detectors configured to receive photons scattered from features of the surface of the article, and a mapping means for mapping the features of the surface of the article. The apparatus is configured to characterize the features of the surface of the article by analyzing the photons received at the plurality of photon detectors. In various embodiments, the photon emitter is configured to emit photons on a portion of the article adjacent to an edge of a data storage area of the surface of the article. In some embodiments, the photon emitter is configured to emit monochromatic light onto the surface edges of the article.

In various embodiments, the mapping means is operable to characterize a feature of the features of the surface of the article as a particle or a defect. In some embodiments, the mapping means is configured to map the location of the features of the surface of the article. In various embodiments, the mapping means is configured to count the features of the surface of the article. In some embodiments, the mapping means is configured to use image processing to determine the locations of each of the features of the article.

Also provided herein is an apparatus, including a detecting means configured to detect one or more particles on a surface edge of an article and a mapping means for mapping the one or more particles on the surface of the article. In various embodiments, the detecting means includes a photon emitter configured to emit photons onto the surface edges of the article and a photon detector array including a plurality of photon detectors configured to receive photons scattered from the one or more particles on the surface edges of the article. In some embodiments, the detecting means is configured to detect the one ore more particles on a portion of the article adjacent to an edge of a data storage area. In various embodiments, the detecting means is configured to use monochromatic light to detect the one or more particles. In some embodiments, the detecting means is configured to use monochromatic light at 20% intensity. In various embodiments, the mapping means is further configured to map one or more defects in the surface edges of the article. In some embodiments, the mapping means is configured to count the one or more particles on the surface edges of the article.

Also provided is an apparatus, including a photon emitting means for emitting photons onto surface edges of an article, a photon detecting means for detecting photons scattered from particles on the surface edges of the article, and a mapping means for mapping a particle or a defect of the surface of the article. In various embodiments, the photon emitting means is configured to emit photons on a portion of the article adjacent to an edge of a data storage area. In some embodiments, the photon emitting means is configured to emit monochromatic light on the surface edges of the article. In various embodiments, the photon emitting means is configured to emit monochromatic parallel light. In some embodiments, the mapping means is configured to count and map the location of one or more particles on the surface edges of the article. In various embodiments, the mapping means is configured to use image processing to determine a location of the particle or the defect of the article.

While particular embodiments have been described and/or illustrated, and while these embodiments and/or examples have been described in considerable detail, it is not the intention of the applicant(s) to restrict or in any way limit the scope of the concepts presented herein to such detail. Additional adaptations and/or modifications may readily appear to persons having ordinary skill in the art, and, in its broader aspects, these adaptations and/or modifications may also be encompassed. Accordingly, departures may be made from the foregoing embodiments and/or examples without departing from the scope of the concepts presented herein, which scope is limited only by the following claims when appropriately construed.

What is claimed is:

1. An apparatus, comprising:
   a photon emitter configured to emit photons onto a surface of an article at a first intensity, wherein the photon emitter is further configured to emit photons onto surface edges of the article at a second intensity that is lower than the first intensity;
   a photon detector array comprising a plurality of photon detectors configured to receive photons emitted from the photon emitter at the second intensity that are scattered from features of the surface edges of the article; and
   a mapping means for mapping the features of the surface edges of the article based on the received photons, wherein the apparatus is configured to characterize the features of the surface edges of the article by analyzing the photons received at the plurality of photon detectors.

2. The apparatus of claim 1, wherein the photon emitter is further configured to emit photons on a surface portion of the article adjacent to a data storage area of the surface of the article.

3. The apparatus of claim 1, wherein the mapping means is operable to characterize a feature of the features of the surface edges of the article as a particle or a defect.

4. The apparatus of claim 1, wherein the photon emitter is configured to emit monochromatic light onto the surface edges of the article.

5. The apparatus of claim 1, wherein the mapping means is configured to map the location of the features of the surface edges of the article.

6. The apparatus of claim 1, wherein the mapping means is configured to count the features of the surface edges of the article.

7. The apparatus of claim 1, wherein the mapping means is configured to use image processing to determine the locations of each of the features of the surface edges of the article.

8. An apparatus, comprising:
   a photon emitter configured to emit photons onto a surface of an article at a first intensity, wherein the photon emitter is further configured to emit photons onto a surface edge of the article at a second intensity that is lower than the first intensity;
   a detecting means configured to detect one or more particles on the surface edge of the article from the photons emitted from the photon emitter at the second intensity; and
   a mapping means for mapping the one or more particles on the surface of the article based on the detected one or more particles.

9. The apparatus of claim 8, wherein the detecting means comprises a photon detector array comprising a plurality of photon detectors configured to receive photons scattered from the one or more particles on the surface edges of the article.

10. The apparatus of claim 8, wherein the mapping means is further configured to map one or more defects in the surface edges of the article.

11. The apparatus of claim 8, wherein the mapping means is configured to count the one or more particles on the surface edges of the article.

12. The apparatus of claim 8, wherein the detecting means is configured to detect the one or more particles on a surface portion of the article adjacent to a data storage area.

13. The apparatus of claim 8, wherein the detecting means is configured to use monochromatic light to detect the one or more particles.

14. The apparatus of claim 13, wherein the detecting means is configured to use monochromatic light at 20% intensity.

15. An apparatus, comprising:
   a photon emitting means for emitting photons onto a surface of an article at a first intensity, wherein the photon emitting means is further for emitting photons onto surface edges of the article at a second intensity that is lower than the first intensity;
   a photon detecting means for detecting photons emitted from the photon emitting means at the second intensity that are scattered from particles on the surface edges of the article; and
   a mapping means for mapping a particle or a defect of the surface of the article based on the detected photons.

16. The apparatus of claim 15, wherein the photon emitting means is configured to emit photons onto a surface portion of the article adjacent to a data storage area.

17. The apparatus of claim 15, wherein the photon emitting means is configured to emit monochromatic light on the surface edges of the article.

18. The apparatus of claim 15, wherein the mapping means is configured to count and map the location of one or more particles on the surface edges of the article.

19. The apparatus of claim 15, wherein the mapping means is configured to use image processing to determine a location of the particle or the defect of the article.

20. The apparatus of claim 15, wherein the photon emitting means is configured to emit monochromatic parallel light.

* * * * *